United States Patent [19]

Dunn et al.

[11] Patent Number: 5,155,269

[45] Date of Patent: Oct. 13, 1992

[54] PURIFICATION OF P-AMINOPHENOL COMPOSITIONS AND DIRECT CONVERSION TO N-ACETYL-P-AMINOPHENOL

[75] Inventors: Thomas J. Dunn, Jefferson County; Vojko B. Jovanovic, St. Charles County, both of Mo.

[73] Assignee: Mallinckrodt, St. Louis, Mo.

[21] Appl. No.: 361,714

[22] Filed: May 24, 1989

Related U.S. Application Data

[63] Continuation of Ser. No. 199,531, May 27, 1988, abandoned, which is a continuation of Ser. No. 53,097, May 22, 1987, abandoned, which is a continuation of Ser. No. 898,054, Aug. 19, 1986, abandoned, which is a continuation of Ser. No. 809,940, Dec. 17, 1985, abandoned, which is a continuation of Ser. No. 575,000, Jan. 30, 1984, abandoned.

[51] Int. Cl.$^5$ .................. C07C 231/24; C07C 231/02; C07C 213/10
[52] U.S. Cl. ..................... 564/144; 564/141; 564/216; 564/223; 564/137; 564/439
[58] Field of Search ............... 564/141, 216, 223, 439, 564/144, 137

[56] References Cited

U.S. PATENT DOCUMENTS 3,845,129  10/1974  Reid ..................................... 564/439
4,440,954   4/1984  Clingan et al. ...................... 564/439

Primary Examiner—Carolyn Elmore
Attorney, Agent, or Firm—Senniger, Powers, Leavitt & Roedel

[57] ABSTRACT

A process for removing impurities from an aqueous feed mixture comprising a reaction solution produced by catalytic hydrogenation of nitrobenzene in an acid aqueous medium. An aqueous feed mixture comprising the reaction solution is contacted with an extractant comprising aniline for extraction from the feed mixture of 4,4'-diaminodiphenylether, thereby providing a primary raffinate that contains p-aminophenol and is contaminated with aniline. The primary raffinate is contacted at a pH of between about 5.5 and about 8.0 with a purifying solvent, the purifying solvent comprising an organic solvent effective for extraction of aniline from the primary raffinate, thereby producing a purified raffinate comprising p-aminophenol.

Also described is a unified process for the preparation of N-acetyl-p-aminophenol in which p-aminophenol contained in the aforesaid purified raffinate is acetylated without prior separation of solid p-aminophenol from the raffinate.

50 Claims, 2 Drawing Sheets

PURIFICATION OF P-AMINOPHENOL COMPOSITIONS AND DIRECT CONVERSION TO N-ACETYL-P-AMINOPHENOL

This application is a continuation of application Ser. No. 199,531, filed May 27, 1988, abandoned which is a continuation of application Ser. No. 053,097, filed May 22, 1987, abandoned, which is a continuation of application Ser. No. 898,054, filed Aug. 19, 1986, abandoned, which is a continuation of application Ser. No. 809,940, filed Dec. 17, 1985, abandoned, which is a continuation of parent application Ser. No. 575,000, filed Jan. 30, 1984, abandoned.

BACKGROUND OF THE INVENTION

This invention relates to the manufacture of N-acetyl-p-aminophenol and more particularly to a improved process in which N-acetyl-p-aminophenol is prepared by acetylation of p-aminophenol that has been produced by catalytic hydrogenation of nitrobenzene in acidic aqueous medium.

N-acetyl-p-aminophenol ("APAP") is an analgesic more commonly known as acetaminophen. Conventionally, APAP is produced by acetylation of p-aminophenol ("PAP") with acetic anhydride. In one variation of this process, the PAP used is produced by catalytic hydrogenation of nitrobenzene in an acidic aqueous medium, for example, in approximately 10% to 15% by weight solution of sulfuric acid.

According to conventional practice, the PAP is first isolated from the hydrogenation reaction medium through precipitation with a base, and the precipitate taken up in a solvent prior to acetylation. Precipitation and redissolution of the PAP has been considered necessary in order to exclude impurities from the acetylation reaction medium. Among the impurities typically present in the PAP reaction liquor are aniline, o-aminophenol, 4,4'-diaminodiphenylether, and other aromatic amines at trace or low levels. Purification of the crude PAP system is necessary to provide for satisfactory manufacture of U.S.P. quality APAP.

In the co-pending and co-assigned application of Clingan et al., Ser. No. 251,461, filed Apr. 20, 1981, U.S. Pat. No. 4,440,954, a process is disclosed for removing 4,4'-diaminodiphenylether from the PAP hydrogenation liquor by extraction with a mixture of aniline and toluene. While this process is quite effective for removing the 4,4'-diaminodiphenylether, residual aniline content in the extract is typically in the range of 25 g/L to 45 g/L. In implementation of the Clingan et al. process, therefore, it has still been considered essential to precipitate PAP from the raffinate by treatment with base, separate the PAP by centrifugation or filtration, and wash the filter cake prior to acetylation.

SUMMARY OF THE INVENTION

Among the several objects of the invention therefore, may be noted the the provision of a process for removal of undesirable impurities, including aniline, from the reaction liquor obtained in the catalytic hydrogenation of nitrobenzene; the provision of an improved process for the preparation of APAP; the provision of a process for the preparation of APAP by acetylation of PAP in a purified catalytic hydrogenation liquor; the provision of a process for producing APAP of high quality; the provision of a process for producing APAP with high yields on PAP and other raw materials; and the provision of a process which simplifies handling of process materials and minimizes the number of process operations in the acetylation of PAP to APAP.

Briefly, therefore, the present invention is directed to an improvement in a process for the preparation of APAP by acetylation of PAP. In the process, PAP is initially prepared by catalytic hydrogenation of nitrobenzene in an aqueous acid medium to produce an aqueous acidic reaction mixture containing PAP, and prior to the conversion of PAP to APAP, by-product 4,4'-diaminodiphenylether is removed from an aqueous feed mixture comprising the aqueous reaction mixture by a primary extraction with an extractant comprising aniline to produce a primary aqueous raffinate containing the PAP reaction product. According to the improvement, the primary raffinate is purified by contacting it at a pH of between about 5.5 and about 8.0 with toluene to extract aniline therefrom and produce a purified raffinate containing PAP dissolved therein.

The invention is further directed to a process for removing impurities from an aqueous feed mixture comprising a reaction solution produced by catalytic hydrogenation of nitrobenzene in an acid aqueous medium. The process comprises contacting the aqueous feed mixture with an extractant comprising aniline for extraction from the feed mixture of 4,4'-diaminodiphenylether, thereby providing a primary raffinate that contains PAP and is contaminated with aniline. The primary raffinate is contacted at a pH of between about 5.5 and about 8.0 with a purifying solvent, the purifying solvent comprising an organic solvent effective for extraction of aniline from the primary raffinate. A purified raffinate comprising PAP is thereby produced.

DESCRIPTION OF THE PREFERRED EMBODIMENTS

In accordance with the present invention, an improved process has been discovered for purifying the PAP reaction liquor obtained upon the catalytic hydrogenation of nitrobenzene in acidic aqueous medium. In a particularly preferred application of the process of the invention, PAP is acetylated in the purified raffinate without prior separation of solid PAP from the raffinate. This unified process reduces the number of process steps and simplifies plant operations, yet provides a product of high quality with favorable yield on PAP and acetic anhydride.

In its preferred embodiments, the process of the invention represents a significant improvement over the process of Clingan et al., Ser. No. 251,461 U.S. Pat. No. 4,440,954. While the Clingan et al. process is effective for removal of 4,4'-diaminodiphenylether and other basic amines from the PAP aqueous reaction liquor by extraction with a mixture of aniline and toluene, the improved process of the invention provides for purification of the aqueous raffinate by extraction to remove residual aniline. It further provides more efficient removal of all impurities in the primary extraction step. The purification step utilizes a solvent which is effective for reducing the aniline content to 2 g/L or less, and thus provides a purified raffinate suitable for direct acetylation.

Figure 1:
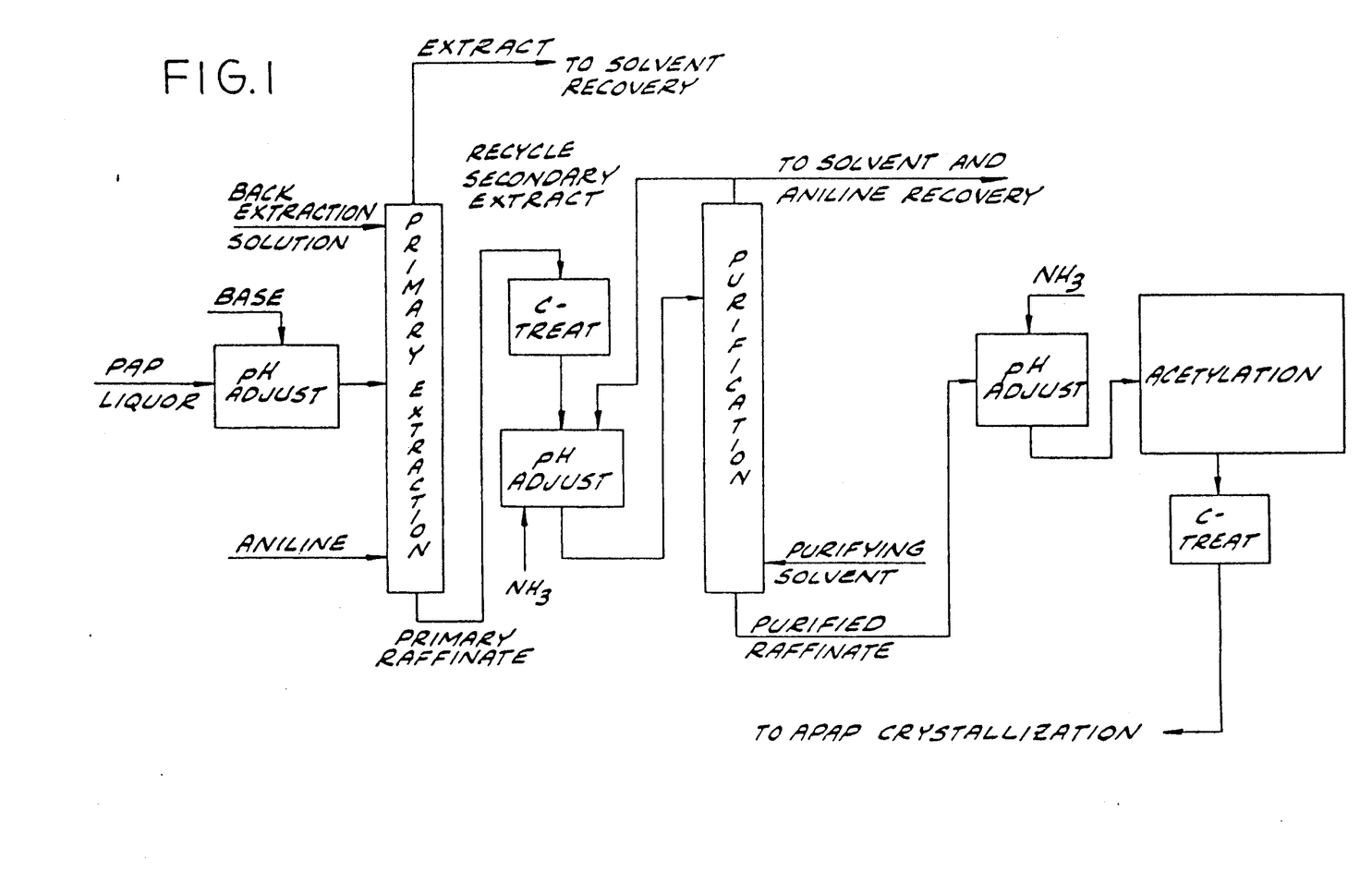
FIG. 1 is a schematic flow sheet illustrating an embodiment of the process of the invention.

In the embodiment of the invention illustrated in FIG. 1, PAP liquor obtained by catalytic hydrogenation of nitrobenzene is adjusted to a pH of 4.0 to 8.0 as, for example, by addition thereto of ammonia or ammonium hydroxide, and the resultant aqueous mixture is extracted with a mixture of aniline and toluene for removal of 4,4'-diaminodiphenylether. As disclosed in the aforesaid Clingan et al. application, the aniline/toluene extractant contains between about 0.2 parts by volume and about 4 parts by volume toluene per part by volume aniline, preferably about 1 part by volume toluene per part by volume aniline. In this extractant mixture, aniline functions as the extracting agent while toluene functions as an anti-solvent and diluent. Extraction of the 4,4'-diaminodiphenylether from the aqueous feed mixture may be carried out on either a batch or on a continuous basis. Preferably, the extraction is carried out in a countercurrent extraction column such as a Karr reciprocating plate extraction column or other similar columns known to those skilled in the art. Equipment such as a centrifugal countercurrent extractor, pumper-decanter, pulsed column, or a mixer/settler apparatus may also be employed. Using a Karr countercurrent extraction column, for example, it has been found that the 4,4'-diaminodiphenylether content of the aqueous PAP phase may be reduced to below 50 ppm and usually below 10 ppm with four to six theoretical extraction stages, using a 50%—50% aniline/toluene mixture with a pH of 4.8. Alternatively, aniline alone may be utilized as the extractant for removal of 4,4'-diaminodiphenylether, but aniline alone results in high PAP losses and phase separation problems. Preferably the volumetric ratio of aniline or aniline/toluene to aqueous feed solution is between about 0.05 and about 1:1, with a ratio of approximately 0.2:1 being preferred.

As illustrated in FIG. 1, the organic extract emanating from the primary extraction step is preferably back-extracted for recovery of the PAP contained therein. Back-extraction is effected by contacting the extract with an aqueous back-extraction solution containing ammonium sulfate, aniline sulfate, or sulfuric acid. Where the primary extraction is carried out in a continuous countercurrent extraction system such as the Karr reciprocating column or other vertical column, back-extraction may be carried out by adding the back extraction solution to the column at a point above the feed point at which the aqueous PAP feed liquor is charged to the column, and withdrawing the back-extracted organic phase from a point above the feed point.

Primary raffinate exiting from the primary extraction step is preferably treated with an adsorbent such as activated carbon for the removal of residual impurities and color. This treatment may be accomplished, for example, by passing the primary raffinate through a fixed bed comprised of the adsorbent.

In accordance with the improved process the primary raffinate, whether treated by adsorption or not, is contacted with a purifying solvent in a liquid-liquid extraction system for extraction of residual aniline to produce a purified raffinate containing PAP dissolved therein. A variety of solvents may be used as the purifying solvent including, for example, halogenated solvents such as ethylene dichloride and methylene dichloride, hydrocarbon solvents such as benzene, toluene, and xylene, as well as various esters of lower alcohols and lower molecular weight alkanoic acids. Hydrocarbon solvents are preferred, with toluene being particularly preferred.

Prior to purification the pH of the primary raffinate is preferably adjusted to between about 5.5 and about 8.0, preferably 6.5 to 7.5, by addition of a base such as ammonia. As pH is increased PAP precipitates, in which case the primary raffinate is in the form of a slurry. Where the purification step is operated at a pH in the preferred range, a portion of the secondary extract is preferably recycled to the pH adjustment point so that pH adjustment takes place in the presence of an organic solvent phase. This stratagem promotes removal of impurities from the aqueous phase simultaneously with precipitation, thereby minimizing occlusions of impurities in the PAP precipitate.

In the purification extraction step, the purifying solvent is preferably mixed with the primary raffinate in a ratio of at least 0.05 part by volume solvent per part by volume aqueous phase, more preferably about 0.1 part by volume solvent per part by volume aqueous phase. Although the purification extraction can be carried out at any temperature between the crystallizing point of the aqueous phase and the boiling point of the solvent at the operating pressure, it is preferred that the extraction be carried out at a temperature of at least about 80° C. to enhance the distribution coefficents and mass transfer rates. A temperature in the range of between about 80° C. and about 85° C. is particularly preferred for operation at atmospheric pressure. Even higher temperatures are advantageous for their favorable effect on the efficiency of extraction, but require the use of pressurized systems.

As in the case of the primary extraction, the purification may be conducted in a batch mixer/settler system, a centrifugal extractor, or a vertical column, with a Karr reciprocating plate column being especially preferred. In such a countercurrent extraction system, approximately six to eight stages are required for lowering the aniline content of the aqueous phase to the extent of producing a purified raffinate containing not more than about 2 g/L of aniline. By carrying out the purifying extraction at relatively high pH, i.e., from about 6.5 to about 7.5, the aniline content of the raffinate can be reduced to as low as about 0.2 g/L. Distribution coefficients between solvent and aqueous phase are more favorable at high pH for both aniline and other aromatic organic amine impurities. Where the primary raffinate contains between about 15 g/L and about 45 g/L of aniline, the secondary extract exiting the purification step typically contains 50 g/L to 300 g/L aniline. Even when the purification is conducted at relatively high pH, PAP losses can be limited to significantly less than 1% by weight where the extract is back-extracted as described above.

Where toluene is used as the purifying solvent, the secondary extract may be recycled and used in the primary extraction step for removal of 4,4'-diaminodiphenylether from the aqueous PAP hydrogenation liquor. Any portion of the secondary extract that is not recycled may be combined with the back-extracted organic phase from the primary extraction step and subjected to distillation for separation of toluene and aniline. The toluene separated in this distillation step may be used as the purifying solvent in the purification extraction step, provided that the aniline content of this toluene fraction has been reduced to no greater than about 0.2% by weight.

Purified raffinate from the purification step can be directly acetylated in the manner outlined in FIG. 1 and described in further detail hereinbelow.

Figure 2:
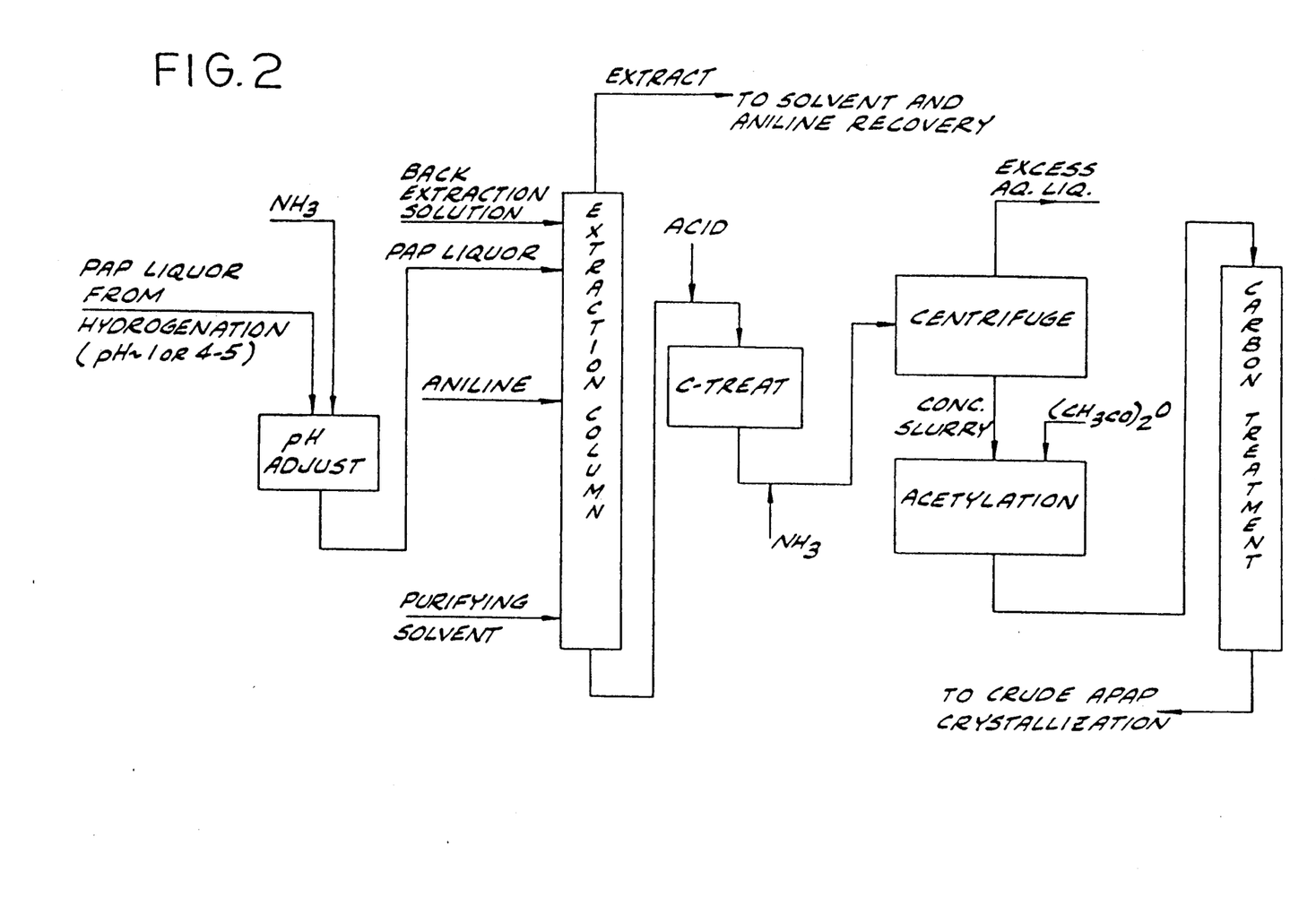
FIG. 2 is a schematic flow sheet illustrating a particularly preferred embodiment of the invention.

FIG. 2 illustrates an alternative and preferred embodiment of the invention in which both the primary and purification extraction operations are carried out in a continuous countercurrent extraction system, preferably a single vertical column, advantageously a Karr reciprocating plate column. As further illustrated in FIG. 2, it is also preferred that the back-extraction be carried out in the same column. In this system, the primary extraction is conducted in a section of the column below the feed point of aqueous PAP liquor and above the point of introduction of aniline or aniline/toluene mixture. Toluene or other purifying solvent is introduced into the column at a point below the point of aniline introduction and the purified raffinate is withdrawn from the column at a point below the point of aniline introduction. Thus, with respect to the flow of the aqueous phase, the purifying solvent is introduced downstream of the point of introduction of aniline. Inasmuch as the purifying solvent necessarily passes through the primary extraction zone of the column, an aniline/toluene primary extractant mixture is present in the primary extraction zone irrespective of whether aniline alone or an aniline/toluene mixture is injected at the point of aniline introduction.

For the back-extraction, an aqueous solution of aniline sulfate, ammonium sulfate, or sulfuric acid is introduced above the PAP liquor feed point and the organic extract is withdrawn above the PAP liquor feed point. The preferred conditions for the primary and purification extraction steps are essentially the same in the process of FIG. 2 as they are in that of FIG. 1, except, of course, that the entire purification extract is necessarily recycled through the primary extraction zone. Prior to extraction, the pH of the aqueous feed liquor is preferably adjusted to at least about 4.0 by addition of a base such as ammonia. Before it passes through the purification extraction zone, the aqueous phase should be adjusted to pH of between about 5.5 and about 8.0, preferably between about 6.5 and about 7.5. In a continuous countercurrent extraction pH adjustment may most easily be carried out prior to feeding the aqueous mixture into the primary extraction zone. However, it may be advantageous to distribute the injection of base over the purification extraction zone, primary extraction zone, or both, in order to provide a pH gradient with a relatively low pH at a point within the zones downstream of the feed point with respect to the flow of aqueous phase. This arrangement minimizes the solubility of PAP in the extract stream as it leaves the primary extraction zone.

Where the pH of the aqueous phase is adjusted to the preferred range of 6.5 to 7.5, PAP contained in the aqueous phase is typically precipitated. Thus, the primary raffinate is in the form of a slurry as it is contacted with the purifying solvent for extraction of aniline in the purification extraction step. If pH adjustment is carried out prior to delivery of the aqueous feed mixture to the extraction column, as is conveniently the case in the system of FIG. 2, a slurry is present in the primary extraction step as well. At a temperature of 80° C. and a pH of about 7, the solids content of the slurry is typically 2% to 7% by weight, preferably 5% to 6% by weight. In accordance with the invention, it has been discovered that each of the liquid/liquid extraction steps can be carried out with high efficiency even where the PAP has been precipitated and is slurried in the aqueous phase. It has further been found that acetic anhydride can be mixed directly with such a slurry and reacted with p-aminophenol contained in the slurry to produce APAP.

As illustrated in FIG. 2, the purified raffinate is preferably subjected to carbon treatment for removal of residual impurities prior to acetylation. Where the primary raffinate is in the form of a slurry, it is acidified to dissolve PAP in the aqueous phase, and the acidified purified raffinate treated with carbon or another adsorbent for removal of impurities. Repurified acidic raffinate exiting the carbon treatment step is preferably treated with a base such as ammonia to reprecipitate the PAP and produce a repurified raffinate slurry in which the acetylation reaction may thereafter be conducted.

Because the acetylation reaction has been found to proceed satisfactorily in a PAP slurry, further gains in productivity may be realized where the slurry is concentrated by partial dewatering prior to introducing acetic anhydride for reaction with the PAP. As shown in FIG. 2, this concentration step is preferably carried out using a solid bowl centrifuge. While this step concentrates the slurry, it does not remove PAP from the aqueous phase within which it is contained. In this fashion, very high payloads of APAP can be obtained.

Irrespective of the pH at which the purification extraction step is carried out, the pH of the purified raffinate or raffinate slurry is preferably adjusted to between about 6 and about 7, preferably between about 6.5 and about 7, prior to acetylation. In the process of the invention, this pH range has been found to provide maximum conversion of PAP to APAP without formation of excessive amounts of impurities. To carry out the acetylation reaction, acetic anhydride is added to the purified or repurified raffinate and the reaction carried out at a temperature of at least about 80° C., preferably between about 85° C. and about 95° C. An approximately 5% to 10% excess of acetic anhydride is preferably used for the acetylation. Substantially quantitative conversion of PAP to APAP is achieved.

After the acetylation reaction is complete, the reaction mixture is preferably treated with an adsorbent for removal of impurities, typically by passing it through a fixed bed of activated carbon. The carbon-treated reaction mixture is then cooled for crystallization of APAP therefrom. Preferably, the mixture is cooled to a temperature of about 15° C., after which the slurry produced upon crystallization is filtered or centrifuged for recovery of the crystalline product. The filter cake is preferably washed with deionized water.

All steps of the processes of both FIG. 1 and FIG. 2 should be maintained under an inert gas blanket, preferably a nitrogen blanket.

In accordance with the invention, it has been found that high quality APAP may be produced in a unified system which does not require recovery of a PAP precipitate for the exclusion of impurities. Good yields are obtained on both PAP and acetic anhydride. In fact, recovery of APAP in the crystallization step is enhanced because solubility of APAP in the crude mother liquor is lower where PAP is acetylated without prior removal from the aqueous phase derived from nitrobenzene hydrogenation. This apparently results from a salting out effect caused by the presence of $(NH_4)_2SO_4$ in the aqueous phase. Additionally, process operations are simplified as compared to the commercial processes previously known to the art.

The following examples illustrate the invention.

EXAMPLE 1

An aqueous PAP liquor produced by the catalytic hydrogenation of nitrobenzene in dilute sulfuric acid solution was subjected to primary extraction in a plant reciprocating plate column for substantial removal of 4,4'-diaminodiphenylether. The raffinate, containing 77.3 g/L PAP, was subjected to further primary extraction (for removal of OAP and other organic amines) and purification extraction (for removal of aniline and other organic amines) in a crosscurrent laboratory extraction system simulating an extraction scheme of the type illustrated in FIG. 1. Prior to laboratory extraction, the PAP liquor at a temperature of 80° C. was passed through a column containing activated carbon and the pH of the liquor was then adjusted from 4.3 to 7.0 by addition of concentrated ammonium hydroxide.

Cross-current extraction was first carried out at 80° C. in five equilibrium stages (primary extraction), using an extractant comprising 50% by volume aniline and 50% by volume toluene. In this extraction system the volumetric ratio of organic-to-aqueous phase was 0.2.

In the second extraction step, primary raffinate emanating from the first step was extracted in five equilibrium stages using toluene as the purifying solvent. The ratio of organic-to-aqueous phase in the second extraction step was 0.1. The aqueous phase contained PAP solids.

All extractions were conducted under a nitrogen blanket. Upon adjustment of pH to 7.0, PAP solids precipatated and were thereafter present as a suspension in the aqueous phase.

The aqueous feed stream and the aqueous and organic phases exiting each of the extraction stages were analyzed for PAP, OAP, aniline, and 4,4'-diaminodiphenylether (ODA). Results of these analyses for the aqueous feed, primary extract, primary raffinate, secondary extract, and purified raffinate are set forth below in Table I.

TABLE I

| SAMPLE | PAP (g/L) | OAP (g/L) | Aniline (g/L) | ODA (g/L) | Other Aromatic Organic Impurities (g/L) |
|---|---|---|---|---|---|
| Aqueous Feed | 77.3 | 1.54 | 35.3 | N.D. | 0.43 |
| Primary Extract | 50.6 | 4.36 | 506 | 0.12 | 4.5 |
| Primary Raffinate | 27.6* | N.D. | 15.3 | N.D. | N.D. |
| Secondary Extract | 6.7 | N.D. | 176 | N.D. | 1.05 |
| Purified Raffinate | 25.1* | N.D. | 0.81 | N.D. | N.D. |

*Reflects analysis for PAP soluble in aqueous phase; solids content of raffinate slurry is not included.

EXAMPLE 2

A PAP liquor obtained by catalytic hydrogenation of nitrobenzene in dilute sulfuric acid was subjected to laboratory extraction simulating a process of the type illustrated in FIG. 2. Concentrated ammonia was added to the PAP liquor at a temperature of 80° C. to adjust the pH of the liquor from 1.2 to 7.0, as a result of which PAP precipitated in the liquor, forming a slurry.

In the first step of the cross-current extraction simulating the primary extraction zone in the extraction column of FIG. 2, the PAP slurry was contacted with an extractant containing 50% by volume aniline and 50% by volume toluene at 80° C. in five equilibrium stages. The organic-to-aqueous volumetric ratio in this step was 0.2. Thereafter the primary raffinate obtained from the first step was subjected to extraction with toluene in six equilibrium stages at an organic-to-aqueous volumetric ratio of 0.1, thus simulating the extraction carried out in the purification zone of the extraction column of FIG. 2.

Samples were taken from the organic and aqueous phases exiting each of the cross-current extraction steps. These samples; were analyzed for PAP, OAP, aniline, and ODA. The results of these analyses of the aqueous feed liqour, primary extract, primary raffinate, secondary extract, and purified raffinate are set forth in Table II.

TABLE II

| SAMPLE | PAP (g/L) | OAP (g/L) | Aniline (g/L) | ODA (g/L) | Other Aromatic Organic Impurities (g/L) |
|---|---|---|---|---|---|
| Aqueous Feed | 79.7 | 1.81 | 28.0 | 2.06 | 6.5 |
| Primary Extract | 50.5 | 5.13 | 481 | 8.48 | 29.24 |
| Primary Raffinate | 28.1* | N.D. | 15.6 | N.D. | N.D. |
| Secondary Extract | 8.82 | 0.58 | 222 | 0.09 | 1.30 |
| Purified Raffinate | 24.7* | N.D. | 0.62 | N.D. | N.D. |

*Reflects analysis for PAP soluble in aqueous phase; solids content of raffinate slurry is not included.

EXAMPLE 3

A portion of the purified raffinate obtained from Example 2 was adjusted to pH 6.5, cooled to between about 15° C. and about 20° C., and concentrated to 240 g/L PAP. Acetic anhydride (110% of stoichiometric equivalent) was added to the concentrated slurry, and the PAP content acetylated at approximately 60° C. The acetylation reaction mixture was treated with activated carbon at between about 95° C. and about 100° C. for removal of residual impurities and then cooled to crystallize the product APAP therefrom. The crystalline product was separated from the mother liquor by filtration and the filter cake analyzed for the presence of various impurities. The results of this analysis are set forth in Table III.

Another portion of the purified raffinate was adjusted to pH 7.0 by addition of ammonia and then concentrated and acetylated as described above. Product APAP was recovered by crystallization and filtration as described above. Analysis of the cake is also set forth in Table III.

TABLE III

CRUDE CAKE COMPOSITION

| Acetylation (pH) | APAP (weight %) | H$_2$O (weight %) | PAP (ppm) | Other Aromatic Organic Impurities (ppm) |
|---|---|---|---|---|
| 6.5 | 99.3 | 0.63 | 80 | 3300 |
| 7.0 | 99.2 | 0.72 | 60 | 4000 |

U.S.P. quality APAP is prepared by recrystallization of the crude APAP.

In view of the above, it will be seen that the several objects of the invention are achieved and other advantageous results attained.

As various changes could be made in the above methods and processes without departing from the scope of the invention, it is intended that all matter contained in the above description or shown in the accompanying drawings shall be interpreted as illustrative and not in a limiting sense.

What is claimed is:

1. In a process for the preparation of N-acetyl-p-aminophenol by acetylation of p-aminophenol, in which the p-aminophenol is initially prepared by catalytic hydrogenation of nitrobenzene in an aqueous acid medium to produce an aqueous acidic reaction mixture containing p-aminophenol and, prior to the conversion of said p-aminophenol to N-acetyl-p-aminophenol, by-product 4,4'-diaminodiphenylether is removed from an aqueous feed mixture comprising said aqueous reaction mixture by a primary extraction with an extractant comprising aniline to produce a primary aqueous raffinate containing the p-aminophenol reaction product, the improvement which comprises purifying the primary raffinate by contacting said raffinate at a pH of between about 6.5 and about 8.0 with a purifying solvent comprising toluene to extract aniline therefrom and produce a purified raffinate containing p-aminophenol dissolved therein.

2. A process as set forth in claim 1 wherein the improvement further comprises reacting acetic anhydride with the p-aminophenol contained in said purified raffinate to produce N-acetyl-p-aminophenol, and recovering N-acetyl-p-aminophenol from the acetylation reaction mixture.

3. An improved process as set forth in claim 1 wherein said 4,4'-diaminodiphenylether is removed from said aqueous feed mixture in a continuous countercurrent extraction system, and said purifying solvent is introduced into the extraction system at a point downstream, with respect to the flow of the aqueous phase, of the point of introduction of aniline into said system.

4. An improved process as set forth in claim 3 wherein countercurrent extraction is carried out in a vertical column, a solvent comprising aniline is introduced into the column at a point below the feed point at which said aqueous feed mixture is introduced into said column, said purifying solvent is introduced into the column below the point of introduction of aniline, and said purified raffinate is withdrawn from the column below the point of introduction of aniline.

5. An improved process as set forth in claim 4 wherein an aqueous solution of a back-extraction agent selected from the group consisting of ammonium sulfate, aniline sulfate, and sulfuric acid is introduced into said column at a point above said feed point, and the extract comprising aniline, said purifying solvent, and 4,4'-diaminophenylether is withdrawn from said column at a point above said feed point, whereby said extract is back-extracted for recovery of p-aminophenyl therefrom.

6. An improved process as set forth in claim 1 wherein a base is added to said reaction mixture of said primary raffinate so that the pH of said primary raffinate is adjusted to between about 6.5 and about 8.0 prior to extraction of with said purifying solvent.

7. An improved process as set forth in claim 6 wherein a base is added to said reaction mixture or said primary raffinate so that the pH of said primary raffinate is adjusted between about 6.5 and about 7.5 prior to extraction with said purifying solvent.

8. An improved process as set forth in claim 1 wherein adjustment of the pH causes precipitation of p-aminophenyl, a primary raffinate slurry containing precipitated p-aminophenol is produced, and said primary raffinate slurry is contacted with said purifying solvent to extract aniline therefrom and produce a purified raffinate slurry containing said p-aminophenol precipitate.

9. An improved process as set forth in claim 8 wherein the pH is adjusted in the presence of an organic solvent.

10. An improved process as set forth in claim 9 wherein secondary extract from the purification extraction is recycled to and mixed with the primary raffinate to provide a source of solvent, the pH of the primary raffinate being adjusted to between about 6.5 and 7.5 as said primary raffinate is mixed with said secondary extract.

11. An improved process as set forth in claim 8 wherein, subsequent to the extraction of aniline with said purifying solvent, acetic anhydride is reacted with the p-aminophenol contained in the aqueous phase to produce N-acetyl-p-aminophenol, said reaction with acetic anhydride being carried out without prior removal of p-aminophenol from said aqueous phase, and N-acetyl-p-phenol is recovered from the acetylation reaction mixture.

12. An improved process as set forth in claim 11 wherein the acetylation reaction is conducted at a pH of between about 6 and about 7.

13. An improved process as set forth in claim 11 wherein said purified raffinate slurry is concentrated by partial dewatering prior to reacting acetic anhydride with the p-aminophenol contained in the slurry.

14. An improved process as set forth in claim 11 wherein, prior to the reaction between acetic anhydride and p-aminophenol, said purified raffinate slurry is acidified to dissolve the p-aminophenol in the aqueous phase, the acidified purified raffinate is treated with an adsorbent for removal of residual impurities therefrom, a base is added to the repurified acidic raffinate to reprecipitate p-aminophenol and produce a repurified raffinate slurry, and the acetylation is conducted by reaction of acetic anhydride and p-aminophenol in said repurified slurry.

15. An improved process as set forth in claim 14 wherein said repurified raffinate slurry is concentrated by partial dewatering prior to reacting acetic anhydride with the p-aminophenol contained in the slurry.

16. An improved process as set forth in claim 6 wherein the extract obtained from said primary extraction is contacted with a back-extraction agent selected from the group consisting of ammonium sulfate, aniline sulfate, and sulfuric acid for extractive recovery of p-aminophenol from said extract.

17. An improved process as set forth in claim 1 wherein said purifying solvent contains not more than about 0.2% by weight aniline.

18. An improved process as set forth in claim 1 wherein said primary raffinate is contacted with said purifying solvent in a ratio of at least about 0.05 parts by volume purifying solvent per part by volume aqueous phase.

19. An improved process as set forth in claim 18 wherein said volumetric ratio is at least about 0.1.

20. An improved process as set forth in claim 18 wherein said purified raffinate contains not more than about 2 g/L aniline.

21. An improved process as set forth in claim 18 wherein the purification extraction is carried out at a temperature of at least about 80° C.

22. A process for removing impurities from an aqueous feed mixture comprising a reaction solution produced by catalytic hydrogenation of nitrobenzene in an acid aqueous medium, the process comprising the steps of:

contacting said aqueous feed mixture with an extractant comprising aniline for extraction from said feed mixture of 4,4'-diaminodiphenylether, thereby providing a primary raffinate that contains p-aminophenol and is contaminated with aniline; and contacting said primary raffinate at a pH of between about 6.5 and about 8.0 with a purifying solvent, said purifying solvent comprising an organic solvent effective for extraction of aniline from said primary raffinate, thereby producing a purified raffinate comprising p-aminophenol.

23. A process as set forth in claim 22 wherein 4,4'-diaminodiphenylether is removed from said aqueous feed mixture in a continuous countercurrent extraction system and said purifying solvent is introduced into the extraction system at a point downstream, with respect to the flow of the aqueous phase, of the point of introduction of aniline into said system.

24. A process as set forth in claim 23 wherein countercurrent extraction is carried out in a vertical column, said solvent comprising aniline is introduced into the column at a point below the feed point at which said aqueous feed mixture is introduced into said column, said purifying solvent is introduced into the column below the point of introduction of aniline and said purified raffinate is withdrawn from the column below the point of introduction of aniline.

25. A process as set forth in claim 22 wherein a base is added to said reaction mixture of said primary raffinate so that the pH of said primary raffinate is adjusted to between about 6.5 and about 8.0 prior to extraction with said purifying solvent.

26. A process as set forth in claim 25 wherein a base is added to said reaction mixture or said primary raffinate so that the pH of said primary raffinate is adjusted to between about 6.5 and about 7.5 prior to extraction with said purifying solvent.

27. A process as set forth in claim 26 wherein adjustment of the pH causes precipitation of p-aminophenol, a primary raffinate slurry containing precipitated p-aminophenol is produced, and said primary raffinate slurry is contacted with said purifying solvent to extract aniline therefrom and produce a purified raffinate slurry containing said p-aminophenol precipitate.

28. A process as set forth in claim 27 wherein the pH is adjusted in the presence of an organic solvent.

29. A process as set forth in claim 28 wherein secondary extract from the purification extraction is recycled to and mixed with the primary raffinate to provide a source of solvent, the pH of the primary raffinate being adjusted to between about 6.5 and about 7.5 as said primary raffinate is mixed with said secondary extract.

30. A process as set forth in claim 27 wherein, subsequent to the extraction of aniline with said purifying solvent, acetic anhydride is reacted with the p-aminophenol contained in the aqueous phase to produce N-phenyl-p-aminophenol, said reaction being carried out without prior removal of p-aminophenol from said aqueous phase, and N-acetyl-p-aminophenol is received from the acetylation reaction mixture.

31. A process as set forth in claim 30 wherein the acetylation mixture is conducted at a pH of between about 6 and about 7.

32. A process as set forth in claim 30 wherein said purified raffinate slurry is concentrated by partial dewatering prior to reacting acetic anhydride with the p-aminophenol contained in the slurry.

33. A process as set forth in claim 30 wherein, prior to the reaction between acetic anhydride and p-aminophenol, said purified raffinate slurry is acidified to dissolve the p-aminophenol in the aqueous phase, the acidified purified raffinate is treated with an adsorbent for removal of residual impurities therefrom, a base is added to the repurified acidic raffinate to reprecipitate p-aminophenol and produce a repurified raffinate slurry, and the acetylation is conducted by reaction of acetic anhydride and p-aminophenol in said repurified slurry.

34. A process as set forth in claim 33 wherein said repurified raffinate slurry is concentrated by partial dewatering prior to reacting acetic anhydride with p-aminophenol contained in the slurry.

35. A process as set forth in claim 25 wherein the pH of said aqueous feed mixture is adjusted to at least about 6.5 prior to extraction with aniline.

36. A process as set forth in claim 35 wherein the pH of said aqueous feed mixture is adjusted to between about 6.5 and about 7.5.

37. A process as set forth in claim 24 wherein an aqueous solution of a back-extraction agent selected from the group consisting of ammonium sulfate, aniline sulfate, and sulfuric acid is introduced into said column at at point above said feed point, and the extract comprising aniline, said purifying solvent, and 4,4'-diaminodiphenylether is withdrawn from said column at a point above said feed point, whereby said extract is back-extracted for recovery of p-aminophenol therefrom.

38. A process as set forth in claim 22 wherein said purifying solvent contains not more than about 0.2% by weight aniline.

39. A process as set forth in claim 22 wherein said primary raffinate is contacted with said purifying solvent in a ratio of at least about 0.05 parts by volume purifying solvent per part by volume aqueous phase.

40. A process as set forth in claim 39 wherein said volumetric ratio is at least about 0.1.

41. A process as set forth in claim 39 wherein said purified raffinate contains not more than about 2 g/L aniline.

42. A process as set forth in claim 22 wherein the countercurrent extraction is carried out at a temperature of at least about 80° C.

43. A process as set forth in claim 22 wherein acetic anhydride is reacted with the p-aminophenol contained in said purified raffinate to produce N-acetyl-p-aminophenol, and N-acetyl-p-aminophenol is recovered from the acetylation reaction mixture.

44. A process as set forth in claim 43 wherein N-acetyl-p-aminophenol is recovered from the acetylation reaction mixture by cooling the acetylation reaction mixture to crystallize N-acetyl-p-aminophenol and separating the crystallized product from the mother liquor.

45. A process as set forth in claim 44 wherein the acetylation reaction mixture is contacted with activated carbon for removal of residual impurities therefrom prior to cooling and crystallization.

46. A process as set forth in claim 22 wherein said extractant comprises aniline and toluene.

47. A process as set forth in claim 46 wherein said extractant contains between about 0.2 parts by volume and about 4 parts by volume toluene per part by volume aniline.

48. In a process for the preparation of N-acetyl-p-aminophenol by acetylation of p-aminophenol, in which p-aminophenol is initially prepared by catalytic hydrogenation of nitrobenzene in an aqueous acid medium to produce an aqueous acidic reaction mixture containing p-aminophenol and, prior to the conversion of said p-aminophenol to N-acetyl-p-aminophenol, by-product 4,4'-diaminophenylether is removed from an aqueous feed mixture comprising said aqueous reaction mixture by a primary extraction with an extractant comprising aniline to produce a primary aqueous raffinate containing the p-aminophenol reaction product, the improvement which comprises purifying the primary raffinate by contacting said raffinate at a pH of between about 6.5 and about 8.0 with a purifying solvent selected from the group consisting of ethylene dichloride, methylene dichloride, benzene, toluene, xylene, and esters of lower alcohols and lower molecular weight alkanoic acids.

49. An improved process as set forth in claim 48 wherein said purifying solvent is selected from the group consisting of toluene and xylene.

50. In a process for the preparation of N-acetyl-p-aminophenol by acetylation of p-aminophenol, in which p-aminophenol is initially prepared by catalytic hydrogenation of nitrobenzene in an aqueous acid medium to produce an aqueous acidic reaction mixture containing p-aminophenol and, prior to the conversion of said p-aminophenol to N-acetyl-p-aminophenol, by-product 4,4'-diaminophenylether is removed from an aqueous feed mixture comprising said aqueous reaction mixture by a primary extraction with an extractant comprising aniline to produce a primary aqueous raffinate containing the p-aminophenol reaction product, the improvement which comprises purifying the primary raffinate by contacting said raffinate at a pH of between about 6.5 and about 8.0 with a solvent consisting essentially of toluene to extract aniline therefrom and produce a purified raffinate containing p-aminophenol dissolved therein.

* * * * *

UNITED STATES PATENT AND TRADEMARK OFFICE
CERTIFICATE OF CORRECTION

PATENT NO. : 5,155,269
DATED : October 13, 1992
INVENTOR(S) : Thomas J. Dunn et al.

It is certified that error appears in the above-identified patent and that said Letters Patent is hereby corrected as shown below:

Column 9, claim 7, line 62, "adjusted between" should read ---adjusted to between---.

Column 10, claim 11, line 21, "N-acetyl-p-phenol" should read ---N-acetyl-p-aminophenol---.

Column 11, claim 25, line 32, "mixture of said" should read ---mixture or said---.

Column 11, claim 30, line 62, "is received" should read ---is recovered---.

Signed and Sealed this

Fifth Day of October, 1993

BRUCE LEHMAN

*Attest:*

*Attesting Officer*

*Commissioner of Patents and Trademarks*